United States Patent
Dai et al.

(10) Patent No.: US 12,415,986 B2
(45) Date of Patent: Sep. 16, 2025

(54) PRODUCTION METHOD FOR NEURON-LIKE CELLS

(71) Applicants: KATAOKA CORPORATION, Kyoto (JP); Kyoto Prefectural Public University Corporation, Kyoto (JP)

(72) Inventors: Ping Dai, Kyoto (JP); Yoshinori Harada, Kyoto (JP); Junichi Matsumoto, Kyoto (JP)

(73) Assignees: Kataoka Corporation, Kyoto (JP); Kyoto Prefectural Public University Corporation, Kyoto (JP)

( * ) Notice: Subject to any disclaimer, the term of this patent is extended or adjusted under 35 U.S.C. 154(b) by 828 days.

(21) Appl. No.: 16/972,834

(22) PCT Filed: Jul. 5, 2019

(86) PCT No.: PCT/JP2019/026777
§ 371 (c)(1),
(2) Date: Dec. 7, 2020

(87) PCT Pub. No.: WO2020/013090
PCT Pub. Date: Jan. 16, 2020

(65) Prior Publication Data
US 2021/0246421 A1    Aug. 12, 2021

(30) Foreign Application Priority Data

Jul. 10, 2018 (JP) ................. 2018-130644

(51) Int. Cl.
*C12N 5/0793* (2010.01)
(52) U.S. Cl.
CPC ........ *C12N 5/0619* (2013.01); *C12N 2501/01* (2013.01); *C12N 2501/40* (2013.01); *C12N 2506/1307* (2013.01)
(58) Field of Classification Search
None
See application file for complete search history.

(56) References Cited

U.S. PATENT DOCUMENTS

| 11,781,108 | B2 | 10/2023 | Dai et al. | |
| 2018/0010092 | A1 | 1/2018 | Dai et al. | |
| 2019/0218516 | A1 | 7/2019 | Murakami et al. | |

FOREIGN PATENT DOCUMENTS

| CN | 107429233 A | 12/2017 | | |
| WO | WO-2016117139 A1 | * | 7/2016 | ............. A61K 35/30 |
| WO | WO-2017027280 A1 | * | 2/2017 | ............. A61K 35/30 |

OTHER PUBLICATIONS

Dai et al. Highly efficient direct conversion of human fibroblasts to neuronal cells by chemical compounds, 2015, Journal of Clinical Biochemistry and Nutrition, 56, pp. 166-170. (Year: 2015).*
Wan et al. Chemical conversion of human lung fibroblasts into neuronal cells (2018) International Journal of Molecular Medicine, 41, pp. 1463-1468. (Year: 2018).*
Dai et al. Method for Producing Nervous System Cells (2016) WO2016117139 (A1), Espacenet English Translation. (Year: 2016).*
Neely et al. DMH1, a Highly Selective Small Molecule BMP Inhibitor Promotes Neurogenesis of hiPSCs: Comparison of PAX6 and SOX1 Expression during Neural Induction (2012) ACS Chemical Neuroscience, 3, pp. 486-487. (Year: 2012).*
Sawai et al. ALK5 i II Accelerates Induction of Adipose-Derived Stem Cells toward Schwann Cells through a Non-Smad Signaling Pathway (2021) Stem Cells International, pp. 1. (Year: 2021).*
National Center for Biotechnology Information (2024) PubChem Compound Summary for CID 449054, RepSox. Retrieved Sep. 24, 2024 from https://pubchem.ncbi.nlm.nih.gov/compound/RepSox. (Year: 2024).*
Voulgaris, Evaluation of Small Molecules for Neuroectoderm differentiation and patterning using Factorial Experimental Design (2016), Master Thesis in Applied Physics, Chalmers University of Technology. (Year: 2016).*
Ping Dai et al., "Highly efficient direct conversion of human fibroblasts to neuronal cells by chemical compounds," Journal of Clinical Biochemistry and Nutrition, vol. 56, No. 3. May 2015, pp. 166-170.
Xiao-Yu Wan et al., "Chemical conversion of human lung fibroblasts into neuronal cells," International Journal of Molecular Medicine, vol. 41, pp. 1463-1468 (2018), Spandidos Publications.

* cited by examiner

*Primary Examiner* — Peter Paras, Jr.
*Assistant Examiner* — Maytee Marie Conte De Jesus
(74) *Attorney, Agent, or Firm* — Morgan, Lewis & Bockius LLP (57) ABSTRACT

It is a main object of the present invention to provide a process for producing a neuron-like cell from a somatic cell, a neuron-like cell obtained thereby, and a composition comprising a combination of chemical substances that can be used for said process without performing artificial gene transfer.
The invention can include, for example, a process for producing neuron-like cells, characterized by comprising a step of culturing somatic cells in the presence of two kinds of inhibitors, i.e., a TGF-β inhibitor and a BMP inhibitor, as well as any three or more selected from the group consisting of four kinds, i.e., a cAMP inducer, a GSK3 inhibitor, an Erk-inhibitor, and a p53-inhibitor, wherein the TGF-β inhibitor is a selective ALK5 inhibitor, and a neuron-like cell obtained by said process.
The neuron-like cells obtained according to the present invention are useful in regenerative medicine and the like.

8 Claims, 4 Drawing Sheets

PRODUCTION METHOD FOR NEURON-LIKE CELLS

CROSS REFERENCE TO RELATED APPLICATIONS

This patent application is a U.S. national-stage application under 35 U.S.C. § 371 of International Patent Application No. PCT/JP2019/026777 filed on Jul. 5, 2019, which claims the benefit of foreign priority to Japanese Patent Application No. JP 2018-130644 filed on Jul. 10, 2018. The International Application was published in Japanese on Jan. 16, 2020, as International Publication No. WO 2020/013090 A1 under PCT Article 21(2).

TECHNICAL FIELD

The present invention is classified to the field of regenerative medicine or direct reprogramming from somatic cells. The present invention relates in the technical field mainly to a process for directly producing neuron-like cells from somatic cells by low molecular weight compounds, and to low molecular weight compound induced neuron-like cells (CiNCs: Chemical compound-induced neuronal cells) produced by such a process. The invention further relates to such neuron-like cells and compositions that can be used for processes of producing such neuron-like cells.

BACKGROUND OF THE INVENTION

Recent developments in cell-related research, particularly in pluripotent cells, have made it possible to obtain therapeutic cells in the quality and quantity available for transplantation into an individual. For several diseases, attempts have been initiated to transplant cells that are effective for treatment into patients.

The cells of the mesenchymal system form various organs of the living body such as muscle, bone, cartilage, bone marrow, fat and connective tissue, and are promising as materials of regenerative medicine. Mesenchymal stem cells (MSCs) are undifferentiated cells present in tissues such as bone marrow, adipose tissue, blood, placentas and umbilical cord. Because of their ability to differentiate into cells belonging to the mesenchymal system, mesenchymal stem cells have attracted attention as a starting material in the production of these cells. Regenerative medicine using mesenchymal stem cells themselves for reconstruction of bone, cartilage, myocardium, etc. is also being investigated.

Meanwhile, methods have also been reported to directly convert somatic cells, such as fibroblasts, to other cells. For example, Non-Patent Document 1 reports that neuron-like cells can be obtained by culturing fibroblasts with six low molecular weight compounds: CHIR99021 (GSK3 inhibitor), PD0325901 (Erk inhibitor), SB431542 (TGF-β inhibitor), LDN193189 (BMP inhibitor), pifithrin-α (p53 inhibitor), and forskolin (cAMP inducer). Patent Document 1 discloses an invention for directly reprogramming human fibroblasts to neuron-like cells in the same manner except for replacing the pifithrin-α (p53 inhibitor) among the above six low molecular weight compounds with dorsomorphin (AMPK inhibitor, BMP inhibitor).

In Non-Patent Document 2 is reported a direct reprogramming from human pulmonary fibroblasts to neuron-like cells by means of a combination of low molecular weight compounds such as valproate (HDAC inhibitor), CHIR99021 (GSK3 inhibitor), RepSox (TGF-β inhibitor), forskolin (cAMP inducer), Y-27632 (ROCK inhibitor), SP600125 (JNK inhibitor), and DMH1 (BMP inhibitor).

PRIOR ART

Patent Document

Patent Document 1: International Publication No. 2018/062269

Non-Patent Document

Non-Patent Document 1: Journal of Clinical Biochemistry and Nutrition, 2015, Vol. 56, No. 3, pp. 166-170
Non-Patent Document 2: International Journal of Molecular Medicine, 2018, 41:1463-1468

SUMMARY OF THE INVENTION

Problem to be Solved by the Present Invention

Direct conversion of somatic cells to desired cells without gene transfer may be an effective option as a means of obtaining therapeutic cells. As for neuron-like cells, like the inventions described in Non-Patent Document 1 or Patent Document 1, although there is a reported example in which it is directly induced from human fibroblasts, it takes about 2 to 3 weeks for the induction, and a process capable of inducing earlier is desired.

It is a main object of the present invention to provide a process for inducing neuron-like cells directly from somatic cells more quickly, i.e., a new process capable of producing neuron-like cells directly from somatic cells more quickly, without performing artificial gene transfer.

Means for Solving the Problems

As a result of intensive studies, the present inventors have found that by using a selective ALK5 inhibitor as a TGF-β inhibitor, direct conversion from somatic cells to neuron-like cells can be performed more quickly, and the present invention has been completed.

The present invention, for example, can include the following.

[1] A process for producing a neuron-like cell, comprising a step of culturing a somatic cell in the presence of a TGF-β inhibitor and a BMP inhibitor, wherein the TGF-β inhibitor is a selective ALK5 inhibitor.

[2] A process for producing a neuron-like cell, comprising a step of culturing a somatic cell in the presence of two kinds of inhibitors: a TGF-β inhibitor and a BMP inhibitor, as well as any three or more selected from the group consisting of four kinds: a CAMP inducer, a GSK3 inhibitor, an Erk inhibitor, and a p53 inhibitor, wherein the TGF-β inhibitor is a selective ALK5 inhibitor.

[3] The process for producing a neuron-like cell according to [1] or [2] above, wherein the BMP inhibitor is an ALK2/3 inhibitor.

[4] The process for producing a neuron-like cell according to any one of [1] to [3] above, wherein the TGF-β inhibitor is RepSox (CAS No.: 446859-33-2) and/or the BMP inhibitor is LDN193189 (CAS No.: 1062368-24-4) and/or dorsomorphin (CAS No.: 866405-64-3).

[5] The process for producing a neuron-like cell according to any one of [1] to [4] above, wherein the CAMP inducer is forskolin (CAS No.: 66428-89-5), the GSK3 inhibitor is CHIR99021 (CAS No.: 252917-06-9), the Erk inhibitor is PD0325901 (CAS No.: 391210-10-9), or the p53 inhibitor is pifithrin-α (CAS No.: 63208-82-2).

[6] The process for producing a neuron-like cell according to any one of [1] to [5] above, wherein the step is a step of culturing a somatic cell in the absence of a growth factor and/or a cytokine.

[7] The process for producing a neuron-like cell according to any one of [1] to [6] above, wherein the step is a step of culturing a somatic cell in the absence of a component involved in a histone.

[8] The process for producing a neuron-like cell according to any one of [1] to [7] above, wherein the somatic cell is a fibroblast.

[9] A neuron-like cell produced from the process for producing a neuron-like cell according to any one of [1] to [8] above.

[10] A composition for producing a neuron-like cell from a somatic cell, comprising a TGF-β inhibitor and a BMP inhibitor, wherein the TGF-β inhibitor is a selective ALK5 inhibitor.

[11] A composition for producing a neuron-like cell from a somatic cell, comprising two kinds of inhibitors: a TGF-β inhibitor and a BMP inhibitor, as well as any three or more selected from the group consisting of four kinds: a cAMP inducer, a GSK3 inhibitor, an Erk inhibitor, and a p53 inhibitor, wherein the TGF-β inhibitor is a selective ALK5 inhibitor.

[12] The composition according to or above, wherein the BMP inhibitor is an ALK2/3 inhibitor.

[13] The composition according to any one of to above, wherein the TGF-β inhibitor is RepSox (CAS No.: 446859-33-2) and/or the BMP inhibitor is LDN193189 (CAS No.: 1062368-24-4) and/or dorsomorphin (CAS No.: 866405-64-3).

[14] The composition according to any one of to above, wherein the CAMP inducer is forskolin (CAS No.: 66428-89-5), the GSK3 inhibitor is CHIR99021 (CAS No.: 252917-06-9), the Erk inhibitor is PD0325901 (CAS No.: 391210-10-9), or the p53 inhibitor is pifithrin-α (CAS No.: 63208-82-2).

[15] The composition according to any one of to above, wherein the somatic cell is a fibroblast.

Effect of the Invention

According to the present invention, neuron-like cells can be produced from somatic cells (particularly fibroblasts) in a shorter period of time than the process described in, for example, Non-Patent Document 1 or Patent Document 1. The neuron-like cells obtained according to the present invention are useful in regenerative medicine and the like.

EMBODIMENT FOR CARRYING OUT THE PRESENT INVENTION

Hereinafter, the present invention will be described in detail.

1 Process for Producing Neuron-Like Cells

The process for producing a neuron-like cell according to the present invention (hereinafter, referred to as "present invention process") comprises a step of culturing a somatic cell in the presence of a TGF-β inhibitor and a BMP inhibitor, wherein the TGF-β inhibitor is a selective ALK5 inhibitor. Alternatively, the present invention process comprises a step of culturing a somatic cell in the presence of two kinds of inhibitors: a TGF-β inhibitor and a BMP inhibitor, as well as any three or more selected from the group consisting of four kinds: a cAMP inducer, a GSK3 inhibitor, an Erk inhibitor, and a p53 inhibitor, wherein the TGF-β inhibitor is a selective ALK5 inhibitor.

In the present invention process, it is preferable that the BMP inhibitor is an ALK2/3 inhibitor. In addition, in the present invention process, it is more preferable that the TGF-β inhibitor is RepSox (CAS No.: 446859-33-2) and/or the BMP inhibitor is LDN193189 (CAS No.: 1062368-24-4) and/or dorsomorphin (CAS No.: 866405-64-3). More preferably, the CAMP inducer is forskolin (CAS No.: 66428-89-5), the GSK3 inhibitor is CHIR99021 (CAS No.: 252917-06-9), the Erk inhibitor is PD0325901 (CAS No.: 391210-10-9), or the p53 inhibitor is pifithrin-α (CAS No.: 63208-82-2).

In the present invention process, it is only necessary to culture a somatic cell in the presence of at least any combination of the above inhibitors, inducers, and the like, and if necessary, the somatic cell may optionally be cultured in the further presence of other inhibitors, inducers, and the like to produce a neuron-like cell.

As for the above inhibitors and inducers, in each of them, either one kind or two or more kinds in combination may be used.

Specific inhibitors and the like may have two or more types of inhibitory effects, and in this case, one inhibitor or the like may be considered to include a plurality of inhibitors and the like.

1.1 Somatic Cells

Cells of an organism can be classified into somatic and germ cells. Any somatic cell can be used as a starting material in the present invention process. The somatic cell is not particularly limited, and may be either a primary cell taken from a living body or a cell from an established cell line. Somatic cells at various stages of differentiation, e.g., terminally differentiated somatic cells, somatic cells on the way to terminal differentiation, or somatic cells that have been initialized and acquired pluripotency, can be used in the present invention process. The somatic cells that can be used in the present invention process include any somatic cells, for example, cells of the hematopoietic system (various lymphocytes, macrophages, dendritic cells, bone marrow cells, etc.), cells derived from organs (hepatocytes, splenocytes, pancreatic cells, kidney cells, lung cells, etc.), cells of the muscle tissue system (skeletal muscle cells, smooth muscle cells, myoblasts, cardiomyocytes, etc.), fibroblasts, neurons, osteoblasts, chondrocytes, endothelial cells, interstitial cells, adipocytes (white adipocytes, etc.), embryonic stem cells (ES cells), etc. The present invention process can also be applied to precursor cells and cancer cells of these cells. Preferably, fibroblasts can be used.

Examples of the source of the above-mentioned somatic cells include, but are not limited to, humans, mammals other than humans, and animals other than mammals (birds, reptiles, amphibians, fishes, and the like). As a source of somatic cells, humans and mammals other than humans are preferred, and humans are particularly preferred. When neuron-like cells are produced by the present invention process for the purpose of administration to humans, preferably, somatic cells harvested from a donor having a matched or similar type of histocompatibility antigen to the recipient can be used. Somatic cells harvested from the recipient itself may be used for the production of neuron-like cells by the present invention process.

1.2 Inhibitors, Etc. According to the Present Invention 1.2.1 TGF-β Inhibitors (Selective ALK5 Inhibitors)

There are three types of TGF-β (transforming growth factor-β), TGF-β1, TGF-β2, and TGF-β3, which are produced from almost all cells. TGF-β suppresses the growth of epithelial cells and many other cells, and thus is involved in a wide variety of cellular functions, including cell growth, transformation, differentiation, development, and control of apoptosis.

In the above three types of TGF-β, ALK5 is also referred to as TGF-β1 receptor. ALK5 is a serine/threonine kinase that forms a heterodimeric complex with the type II TGF-β receptor upon binding to TGF-β, which transduces TGF-β signals from the cell surface to the cytoplasm.

In the present invention, "in the presence of a TGF-β inhibitor" is synonymous with "in the presence of a selective ALK5 inhibitor" because the present invention is characterized in that a selective ALK5 inhibitor is used among TGF-β inhibitors.

The term "in the presence of a selective ALK5 inhibitor" refers to a culture condition capable of almost exclusively inhibiting ALK5, and the means is not particularly limited, and any means capable of almost exclusively inhibiting ALK5 can be used. In the present invention, it is possible to use a substance (e.g., an anti-ALK5 antibody or other agent) which exclusively and directly acts on ALK5 to inhibit its function, an agent which exclusively suppresses the production of ALK5 per se, and the like. It is also possible to inhibit ALK5-mediated signaling upstream of it, provided that it is possible to exclusively inhibit ALK5.

Thus, even if it is a TGF-β inhibitor, such inhibitors like SB431542 (CAS No.: 301836-41-9) and A83-01 (CAS No.: 909910-43-6) that broadly inhibit ALK4 and 7 in addition to ALK5 are not included in the TGF-β inhibitors according to the present invention.

The selective ALK5 inhibitor which can be used in the present invention is not particularly limited as long as it can exhibit its function, and examples thereof include the following RepSox.

RepSox (ALK5 Inhibitor, CAS No.: 446859-33-2)

[Chemical 1]

In the present invention, the concentration of the selective ALK5 inhibitor may be appropriately determined, and is not particularly limited, and may be used, for example, in a range of 0.1 μmol/L to 30 μmol/L, preferably in a range of 0.5 μmol/L to 10 μmol/L.

1.2.2 BMP Inhibitors

BMP (Bone Morphogenetic Protein) is a growth factor belonging to TGF-β superfamily and regulates embryonic and tissue development, cell differentiation, cell death, and so on. BMP binds to type I and type II receptors on the plasma membrane to form a heterotetramer, which transduces BMP signals into the nucleus via phosphorylation of the transcription factor SMAD. Many BMP inhibitors inhibit the phosphorylation of SMAD by a type I receptor ALK (Activin receptor-like kinase)-2,3,6 activated by BMP binding.

Among the above ALKs, ALK2 is a receptor serine/threonine kinase of ALK family members, located upstream of signaling pathways involving SMAD proteins, particularly SMAD1/5/8. Endoglin reduces the motility of prostatic carcinoma cells through activation of ALK2-Smad1 pathway. ALK2 gene is a major gene involved in fibrodysplasia ossificans progressiva (FOP), an unusual autosomal dominant congenital disorder characterized by progressive heterotopic bone formation in muscle tissue.

ALK3 is a member of the transmembrane serine/threonine kinase family. ALK3 gene acts as a minor susceptibility gene in PTEN (phosphatase and tensin homologue deleted on chromosome 10) mutation-negative Cowden's disease. ALK3 trafficking plays key roles in the pathogenesis of FOPs and is also involved in human T-cell differentiation.

The term "in the presence of a BMP inhibitor" refers to a culture condition capable of inhibiting the BMP signaling pathway, and the means thereof is not particularly limited, and any means capable of inhibiting the BMP signaling pathway can be used. The present invention can use substances that directly act on BMPs and BMP receptors to inhibit their function (e.g., anti-BMP antibodies, other drugs), or agents that suppress their expression. It is also possible to inhibit the BMP signaling pathway by inhibiting the expression of SMAD transcription factors downstream of signaling involving BMPs and their post-translational modifications.

In the present invention, somatic cells are cultured in the presence of a BMP inhibitor, and it is preferable to culture somatic cells in the presence of an ALK2/3 inhibitor among BMP inhibitors.

The term "in the presence of an ALK2/3 inhibitor" refers to a culture condition capable of inhibiting both ALK2 and 3, and the means thereof is not particularly limited, and any means capable of inhibiting both ALK2 and 3 can be used. In the present invention, a substance which directly acts on both of ALK2 and 3 to inhibit their function (e.g., an anti ALK2/3 antibody or other agents), an agent which inhibits the production of ALK2 and 3 themselves, and the like can be used. Also, provided that both ALK2 and 3 can be inhibited, ALK2 and 3 may be inhibited upstream thereof.

The BMP inhibitor or ALK2/3 inhibitor which can be used in the present invention is not particularly limited as long as it can exhibit its function, and examples thereof include the following compounds. Preferably, mention may be made of LDN193189 and dorsomorphin, which are ALK2/3 inhibitors.

LDN193189 (CAS No.: 1062368-24-4)

[Chemical 2]

Dorsomorphin (also called AMPK Inhibitor, Compound C) (CAS No.: 866405-64-3)
Dorsomorphin dihydrochloride (CAS No.: 1219168-18-9)
DMH1 (CAS No.: 1206711-16-1)
K02288 (CAS No.: 1431985-92-0)
LDN212854 (CAS No.: 1432597-26-6)
LDN193189 HCl (CAS No.: 1062368-62-0)
ML347 (CAS No.: 1062368-49-3)
LDN214117 (CAS No.: 1627503-67-6)

In the present invention, the concentration of the BMP inhibitor or ALK2/3 inhibitor may be appropriately determined, and is not particularly limited, and may be used, for example, in the range of 0.1 µmol/L to 10 µmol/L, preferably 0.5 µmol/L to 5 µmol/L.

1.2.3 cAMP-Inducers

CAMP (cyclic adenosine monophosphate) is a second messenger that is involved in a variety of intracellular signaling events. CAMP is produced intracellularly by cyclization of adenosine triphosphate (ATP) by adenylyl cyclase (adenylate cyclase).

The term "in the presence of a cAMP inducer" refers to a culture condition capable of inducing cAMP, and the means thereof is not particularly limited, and for example, any means capable of increasing the intracellular cAMP level can be used. Substances that can induce cAMP by acting directly on adenylyl cyclase, an enzyme involved in the production of cAMP, substances that can promote the expression of adenylyl cyclase, and substances that inhibit phosphodiesterase, an enzyme that degrades cAMP, can be used as measures to increase intracellular CAMP concentrations. It is also possible to use dibutyryl cAMP, a structural analogue of cAMP, which has the same effect as CAMP in cells.

The CAMP-inducer which can be used in the present invention is not particularly limited as long as it can exhibit its function, and examples thereof include forskolin (CAS No.: 66575-29-9), and forskolin derivatives (e.g., JP 2002-348243) and the following compounds. Preferably, forskolin can be used.

Forskolin (CAS No.: 66428-89-5)

[Chemical 3]

Isoproterenol (CAS No.: 7683-59-2)
NKH477 (CAS No.: 138605-00-2)
PACAP1-27 (CAS No.: 127317-03-7)
PACAP1-38 (CAS No.: 137061-48-4)

In the present invention, the concentration of the CAMP inducer may be appropriately determined, and is not particularly limited, and may be used, for example, in a range of 0.2 µmol/L to 50 µmol/L, preferably in a range of 1 µmol/L to 30 µmol/L.

1.2.4 GSK3 Inhibitors

GSK3 (glycogen synthase kinase-3) was found as a protein kinase that phosphorylates and inactivates glycogen synthase. In mammals, GSK3 is classified into two isoforms: 51 kDa α (GSK3α) and 47k Da β (GSK3β). GSK3 has the activity of phosphorylating various proteins and is involved not only in glycogen metabolism but also in physiological phenomena such as cell division and cell growth.

The term "in the presence of a GSK3 inhibitor" refers to a culture condition capable of inhibiting GSK3, and the means thereof is not particularly limited, and substances that inhibit the activity of GSK3, for example, GSK3 signal inhibiting means such as anti-GSK3 antibodies and GSK3 inhibitors can be used. Because GSK3 loses its activity when phosphorylated at certain sites, the above-described phosphorylation-promoting measures can also be used to inhibit GSK3 signaling.

The GSK3 inhibitor which can be used in the present invention is not particularly limited as long as it can exhibit its function, and examples thereof include the following compounds. Preferably, mention may be made of CHIR99021.

CHIR99021 (CAS No.: 252917-06-9)

[Chemical 4]

BIO ((2'Z,3'E)-6-Bromoindirubin-3'-oxime) (CAS No.: 667463-62-9)
Kenpaullone (CAS No.: 142273-20-9)
A1070722 (CAS No.: 1384424-80-9)

SB216763 (CAS No.: 280744-09-4)
CHIR98014 (CAS No.: 556813-39-9)
TWS119 (CAS No.: 601514-19-6)
Tideglusib (CAS No.: 865854-05-3)
SB415286 (CAS No.: 264218-23-7)
Bikinin (CAS No.: 188011-69-0)
IM-12 (CAS No.: 1129669-05-1)
1-Azakenpaullone (CAS No.: 676596-65-9)
LY2090314 (CAS No.: 603288-22-8)
AZD1080 (CAS No.: 612487-72-6)
AZD2858 (CAS No.: 486424-20-8)
AR-A014418 (CAS No.: 487021-52-3)
TDZD-8 (CAS No.: 327036-89-5)
Indirubin (CAS No.: 479-41-4)

In the present invention, the concentration of the GSK3 inhibitor may be appropriately determined, and is not particularly limited, and may be used, for example, in a range of 0.1 μmol/L to 20 μmol/L, preferably in a range of 0.5 μmol/L to 10 μmol/L.

1.2.5 Erk Inhibitors

Erk is a subfamily of MAPK that is activated by EGF (Epidermal Growth Factor), serum-stimulation, or oxidative stress, and Erk is divided into ERK1/2, ERK5, ERK7, ERK8 based on differences in the signal transduction pathways in which they are involved. Ligand-binding to tyrosine kinase receptors, such as the epidermal growth factor receptor (EGFR), results in signal flow, which phosphorylates and activates TEY-motifs present in the activation loops of Erk.

The term "in the presence of an Erk inhibitor" refers to a culture condition capable of inhibiting Erk, and the means thereof is not particularly limited, and a substance that inhibits the activity of Erk, for example, an Erk signal inhibiting means such as an anti-Erk antibody or an Erk inhibitor, can be used. Means for inhibiting enzymes involved in the activation of Erk, such as Erk kinase and Erk kinase kinase, can also be used for Erk inhibition.

The Erk inhibitor which can be used in the present invention is not particularly limited as long as it can exhibit its function, and examples thereof include the following compounds. Preferably, mention may be made of PD0325901.

PD0325901 (CAS No.: 391210-10-9)

[Chemical 5]

Olomoucine (CAS No.: 101622-51-9)

[Chemical 6]

Aminopurvalanol A (CAS No.: 220792-57-4)

[Chemical 7]

AS703026 (CAS No.: 1236699-92-5)
AZD8330 (CAS No.: 869357-68-6)
BIX02188 (CAS No.: 334949-59-6)
BIXO2189 (CAS No.: 1265916-41-3)
C1-1040 (CAS No.: 212631-79-3)
Cobimetirlib (CAS No.: 934660-93-2)
GDC-0623 (CAS No.: 1168091-68-6)
MEK162 (CAS No.: 606143-89-9)
PD318088 (CAS No.: 391210-00-7)
PD98059 (CAS No.: 167869-21-8)
Refametinib (CAS No.: 923032-37-5)
RO4987655 (CAS No.: 874101-00-5)
SCH772984 (CAS No.: 942183-80-4)
Selumetinib (CAS No.: 606143-52-6)
SL327 (CAS No.: 305350-87-2)
Trametinib (CAS No.: 871700-17-3)
ARRY-142886 (CAS No.: 606143-52-6)
XL518 (CAS No.: 934660-93-2)
RDEA119 (CAS No.: 923032-38-6)

In the present invention, the concentration of the Erk inhibitor may be appropriately determined, and is not particularly limited, and may be used, for example, in a range of 0.1 μmol/L to 10 μmol/L, preferably 0.2 μmol/L to 5 μmol/L.

1.2.6 p53 Inhibitors p53 is one of the most important tumor suppressor genes, which suppresses cell proliferation and plays an important role in tumor suppression. And, p53 activates its target genes in response to various stresses, and becomes an origin for cell cycle arrest, apoptosis, DNA repair, cell senescence, etc.

The term "in the presence of a p53 inhibitor" refers to a culture condition capable of inhibiting p53, and the means thereof is not particularly limited, and any means capable of inhibiting p53 can be used. In the present invention, a substance which acts directly on p53 to inhibit its function (e.g., an anti-p53 antibody, other agents), an agent which suppresses the production of p53 itself, and the like can be used. It is also possible to inhibit p53 by inhibiting p53-mediated signaling upstream thereof.

The p53 inhibitor which can be used in the present invention is not particularly limited as long as it can exhibit its function, and for example, the following compounds can be used. Preferably, pifithrin or pifithrin-α can be used.

Pifithrin-α (CAS No.: 63208-82-2)

[Chemical 8]

Pifithrin-β (CAS No.: 511296-88-1)
Pifithrin-μ (CAS No.: 64984-31-2)
NSC66811 (CAS No.: 6964-62-1)
Nultin-3 (CAS No.: 548472-68-0)

In the present invention, the concentration of the p53 inhibitor may be appropriately determined, and is not particularly limited, and may be used, for example, in a range of 0.5 μmol/L to 30 μmol/L, preferably from 1 μmol/L to 10 μmol/L.

1.3 Other Preferred Conditions

Although not particularly limited in the present invention, it is preferable to culture somatic cells in the absence of growth factors and/or cytokines in the manufacturing process. Absence of growth factor and/or cytokine means substantial absence of growth factor and/or cytokine, and includes not only the absence of any growth factor and/or cytokine, but also the presence of trace amounts of growth factor and/or cytokine. Advantages of culturing somatic cells in the absence of growth factors and/or cytokines include the ability to inexpensively produce neuron-like cells.

A growth factor is a generic term for an endogenous protein that promotes the proliferation and differentiation of specific cells in vivo. Cytokines are proteins secreted by cells of the immune system, and are responsible for signal transduction in unspecified target cells. Many cytokines are related to immunity and inflammation, and others are related to cell proliferation, differentiation, cell death, or wound healing. Some growth factors are included in cytokines, and they are not mutually exclusive concepts.

Growth factors include epidermal growth factor (Epidermal Growth Factor: EGF), insulin-like growth factor (Insulin-like Growth Factor: IGF), transforming growth factor (Transforming Growth Factor: TGF), nerve growth factor (Nerve Growth Factor: NGF), vascular endothelial growth factor (Vascular Endothelial Growth Factor: VEGF), basic fibroblast growth factor (basic Fibroblast Growth Factor: bFGF), and hepatocyte growth factor (Hepatocyte Growth Factor: HGF).

Cytokines include interleukins (Interleukin: IL), interferons (Interferon: IFN), leptins (leptin), and the like.

Although not particularly limited in the present invention, it is preferable to culture somatic cells in the absence of components involved in histones in the manufacturing process. Absence of a histone-related component means substantial absence of a histone-related component, and is intended to include not only the absence of any histone-related component, but also the presence of trace amounts of a histone-related component. Components involved in histones may include, for example, histone deacetylase inhibitors (e.g., valproic acid). Without the use of histone deacetylase inhibitors, which are said to promote reprogramming by nuclear initialization factors, the risk of inducing pluripotent cells that could cause unintended differentiation is lower.

1.4 Somatic Cell Culture

Culturing of somatic cells in the present invention process may be carried out by selecting a medium, a temperature, or other conditions depending on the type of somatic cells to be used, and in the presence of various inhibitors (and, optionally, an inducer or an activator) described above. The medium may be selected from a known medium or a commercially available medium. For example, commonly used media such as MEMs (Minimum Essential Medium), DMEM (Dulbecco's Modified Eagle's Medium), and DMEM/F12, or a modified medium thereof can be used with an addition of appropriate components (sera, proteins, amino acids, saccharides, vitamins, fatty acids, antibiotics, and the like) to the medium.

In the present invention, neuron-like cells are produced from somatic cells. Brain-derived neurotrophic factor (BDNF: Brain-Derived Neurotrophic Factor), glial cell-derived neurotrophic factor (GDNF: Glial cell-Derived Neurotrophic Factor), cAMP, ascorbic acid, ascorbic acid-2-phosphate, and the like are known to be effective agents for inducing differentiation into neuron-like cells. As an effective substance for inducing differentiation into neuron-like cells, for example, those commercially available as differentiation inducers can also be used. In the present invention, a somatic cell may be cultured in the presence of the above-described substance.

As a culture condition, a general condition of cell culture may be selected. Examples include 37° C. and 5% $CO_2$. It is preferred to change the medium at appropriate intervals during culture (preferably once per 1 to 7 days, more preferably once per 3 to 4 days). When the present invention process is carried out using fibroblasts as materials, neuron-like cells appear in 4 days to 1 week under conditions of 37° C. and 5% $CO_2$. It is also possible to convert somatic cells that have previously been increased in number into neuron-like cells by selecting easily culturable ones as the somatic cells to be used. Thus, the scaled-up production of neuron-like cells is also easy.

For culturing somatic cells, a cell culture container such as a plate, a dish, a flask for cell culture, a bag for cell culture, or the like can be used. Note that, as the bag for cell culture, one having gas permeability is suitable. Large culture vessels may be used when large amounts of cells are required. The culture can be carried out in either an open system or a closed system, but when the purpose is administration or the like of the obtained neuron-like cells to a human or the like, it is preferable to carry out the culture in a closed system.

In the present invention process, a neuron-like cell can be produced from a somatic cell by a one-step culture by culturing a somatic cell in a medium containing various inhibitors and the like described above.

1.5 Neuron-Like Cells

By the above-described present invention process, a cell population containing neuron-like cells can be obtained. The neuron-like cells produced by the present invention process are also within the scope of the present invention. Examples of the neuron-like cells produced by the present invention process include, but are not limited to, nerve cells (neurons), glial cells (astrocytes, oligodendrocytes, microglia), Schwann cells, and the like. In addition to the terminally differentiated cells described above, they may also be progenitor cells destined to differentiate into neuron-like cells.

The neuron-like cells produced by the present invention process can be identified, for example, by morphological changes in cells. Since neuron-like cells have characteristic morphologies depending on the type of cell, the presence of neuron-like cells can be recognized by comparing the morphologies of the cells before and after culturing. Molecules characteristic of neuron-like cells, such as enzymes, receptors, or low molecular weight compounds, can also be detected to identify neuron-like cells. Molecules characteristic of neuron-like cells include, but are not limited to, β3-tubulin, synapsin I, vesicle-type glutamate transporter (vesicular glutamate transporter: vGULT), microtubule-associated proteins (microtubule-associated protein: MAP) 2, γ-aminobutyric acid (GABA), tyrosine hydroxylase, and the like.

Quarantine methods (detection with antibodies) can be used for detection of the above molecules, but detection of protein molecules may be performed with quantitation of mRNA quantities thereof. Antibodies that recognize molecules characteristic of neuron-like cells are also useful in isolating and purifying the neuron-like cells obtained by the present invention process.

The neuron-like cells produced by the present invention process are useful, for example, in the treatment of nervous system diseases. The nervous system diseases include, but are not limited to, spinal cord injury, cerebrovascular disorders (e.g., cerebral infarction), Parkinson's disease, Alzheimer's disease, amyotrophic lateral sclerosis, and the like. The neuron-like cells produced in the present invention process can be used to produce pharmaceutical compositions for the treatment of nervous system diseases.

When the neuron-like cells produced by the present invention process are used as pharmaceutical compositions, the neuron-like cells may be mixed with a pharmaceutically acceptable carrier or the like by a conventional method to prepare a formulation suitable for administration to an individual. Examples of the carrier include saline, distilled water for injection made isotonic with glucose or other adjuvants (e.g., D-sorbitol, D-mannitol, sodium chloride, and the like). Further, buffers (e.g., phosphate buffer, sodium acetate buffer), analgesics (e.g., benzalkonium chloride, procaine hydrochloride), stabilizers (e.g., human serum albumin, polyethylene glycol), preservatives, antioxidants, and the like may be blended.

The neuron-like cells produced by the present invention process may further be a composition in combination with other cells or components which are effective for the functional exertion or the improvement of engraftment of neuron-like cells.

Further, the neuron-like cells produced by the present invention process can also be used for screening of drug candidate compounds that act on neuron-like cells and for safety evaluation of the drug candidate compounds. According to the present invention process, since large quantity of neuron-like cells can be obtained in a single operation, it is possible to obtain reproducible research results without being affected by a lot difference of cells.

2 Composition

The composition according to the present invention (hereinafter, referred to as "present invention composition") is a composition for producing a neuron-like cell from a somatic cell, comprising a TGF-β inhibitor and a BMP inhibitor, and being characterized in that the TGF-β inhibitor is a selective ALK5 inhibitor. Alternatively, the present invention composition comprises two kinds of inhibitors: a TGF-β inhibitor and a BMP inhibitor, as well as any three or more selected from the group consisting of four kinds: a cAMP inducer, a GSK3 inhibitor, an Erk inhibitor, and a p53 inhibitor, and being characterized in that the TGF-β inhibitor is a selective ALK5 inhibitor.

In the present invention composition, the BMP inhibitor is preferably an ALK2/3 inhibitor. In addition, in the present invention composition, it is preferable that the TGF-β inhibitor is RepSox (CAS No.: 446859-33-2) and/or the BMP inhibitor is LDN193189 (CAS No.: 1062368-24-4) and/or dorsomorphin (CAS No.: 866405-64-3). More preferably, the cAMP inducer is forskolin (CAS No.: 66428-89-5), the GSK3 inhibitor is CHIR99021 (CAS No.: 252917-06-9), the Erk inhibitor is PD0325901 (CAS No.: 391210-10-9), or the p53 inhibitor is pifithrin-α (CAS No.: 63208-82-2).

In the present invention composition, at least any of the above inhibitors, inducers, and the like may be contained, and if necessary, other inhibitors, inducers, and the like may optionally be further included.

As for the above inhibitors and inducers, in each of them, either one kind or two or more kinds in combination may be used.

Specific inhibitors and the like may have two or more types of inhibitory effects, and in this case, one inhibitor or the like may be considered to include a plurality of inhibitors and the like.

Specific examples and preferred examples of the above-mentioned inhibitors and inducers and the like are synonymous with those described above.

The present invention composition can be used as compositions for producing a neuron-like cell from a somatic cell. The present invention composition can also be used as a medium for producing a neuron-like cell from a somatic cell.

Examples of the medium used for the production of neuron-like cells from somatic cells include a medium in which a selective ALK5 inhibitor, which is one of TGF-β inhibitors, and a BMP inhibitor (preferably ALK2/3 inhibitor), or in addition to these, any three or more selected from the group consisting of four kinds: a cAMP inducer, a GSK3 inhibitor, an Erk inhibitor, and a p53 inhibitor are contained as active ingredients in a basal medium prepared by mixing components required for cell culture. The active ingredients described above may be contained in a concentration effective for producing a neuron-like cell, and the concentration may be appropriately determined by one skilled in the art. The basal medium may be selected from known or commercially available media. For example, a common medium, MEM (Minimum Essential Medium), DMEM (Dulbecco's Modified Eagle's Medium), DMEM/F12, or a medium modified therefrom, can be used as a basal medium.

The medium may further be supplemented with known medium components described above herein, e.g., sera, proteins (albumin, transferrin, growth factor, etc.), amino acids, saccharides, vitamins, fatty acids, antibiotics, and the like.

The medium may further be supplemented with substances effective for induction of differentiation into neuron-like cells, such as brain-derived neurotrophic factor (BDNF: Brain-Derived Neurotrophic Factor), glial-cell-derived neurotrophic factor (GDNF: Glial cell-Derived Neurotrophic Factor), cAMP, ascorbic acid, ascorbic acid-2-phosphate, and the like, as described hereinabove.

Further, in the present invention, for example, it is also possible to produce a neuron-like cell from a somatic cell in vivo by administering to a living organism a composition which contains a selective ALK5 inhibitor, which is one of TGF-β inhibitors, and a BMP inhibitor (preferably an ALK2/3 inhibitor), or in addition to these, any three or more selected from the group consisting of four kinds: a cAMP inducer, a GSK3 inhibitor, an Erk inhibitor, and a p53 inhibitor. That is, according to the present invention, there is provided, for example, a process for manufacturing a neuron-like cell from a living body comprising administering to a living organism a composition which contains a selective ALK5 inhibitor, which is one of TGF-β inhibitors, and a BMP inhibitor (preferably ALK2/3 inhibitor), or in addition to these, any three or more selected from the group consisting of four kinds: a cAMP inducer, a GSK3 inhibitor, an Erk-inhibitor, and a p53-inhibitor. Preferred combinations of such inhibitors to be administered to a living body are as described herein.

Further, as the living organism, a human, a mammal other than a human, and an animal other than a mammal (birds, reptiles, amphibians, fish, and the like) are exemplified, but humans are particularly preferred. For example, a neuron-like cell can be manufactured from a somatic cell at a specified site by administration to the specific site in a living organism of a composition containing a selective ALK5 inhibitor, which is one of TGF-β inhibitors, and a BMP inhibitor (preferably an ALK2/3 inhibitor), or in addition to these, any three or more selected from the group consisting of four kinds: a CAMP inducer, a GSK3 inhibitor, an Erk inhibitor, and a p53 inhibitor.

EXAMPLES

Hereinafter, the present invention will be specifically illustrated by way of Examples, but the present invention is not limited to the scope of the Examples.

Example 1: Production of Neuron-Like Cells (1) Human Fibroblasts

The human fibroblasts used as the material were purchased from DS Pharma Biomedical Co., Ltd. The fibroblasts are derived from 38-year-old human skin.

(2) Direct Induction from Human Fibroblasts to Neuron-Like Cells

Human fibroblasts were seeded at $8 \times 10^4$ cells per 35-mm dish and cultured in DMEM high glucose medium (manufactured by Wako Pure Chemical Industries) supplemented with 10% fetal bovine serum (Fetal bovine serum; FBS), 100 U/ml penicillin, and 100 μg/ml streptomycin for 3 days at 37° C. under 5% $CO_2$ conditions. Note that DMEM means Dulbecco's Modified Eagle's Medium.

The medium for the above dishes of human fibroblasts was changed to an IMDM medium (Cat #: 12440053, manufactured by Gibco Co.) supplemented with 5% fetal bovine serum (FBS, manufactured by Hyclone Co.), ITS-X (Cat #: 51500056, manufactured by Gibco), non-essential amino acids (NEAA: Non-essential amino acids; Cat #: 11140050, manufactured by Gibco), nicotinamide (Cat #: 72340-100G, manufactured by Sigma-Aldrich Co.; final concentration of 5 mmol/L), Dexamethasone (Cat #: 047-18863, manufactured by Wako Pure Chemical Industries Co.; final concentration of 0.1 μmol/L), 100 U/ml penicillin, 100 μg/ml streptomycin, and the following cytokines and low molecular weight compounds. After that, the medium was changed every three days to the medium having the same composition, and the culture was carried out at 37° C. under 5% $CO_2$ conditions.

The medium for the above dishes of human fibroblasts was changed to a medium supplemented with a 0.5% N-2 supplement (manufactured by Thermo Fisher Scientific), 1% B-27 supplement (manufactured by Thermo Fisher Scientific), 50% DMEM/F12, 50% Neurobasal Medium (manufactured by Thermo Fisher Scientific), and low molecular weight compounds added in accordance with Tables 1 and 2. After that, the medium was changed every three days to the medium having the same composition, and the culture was performed at 37° C. under 5% $CO_2$ conditions. Details of the compounds shown in Tables 1 and 2 are as described above herein.

TABLE 1

(Unit: μmol/L)

| Compound | Function | Example 1 | Example 2 | Example 3 | Example 4 | Example 5 | Example 6 | Example 7 | Example 8 |
|---|---|---|---|---|---|---|---|---|---|
| RepSox | TGF-β inhibition (Selective ALK5 inhibition) | 2 | 2 | 2 | 2 | 2 | 2 | 2 | 2 |
| SB431542 | TGF-β inhibition (ALK4, 5, 7 inhibition) | — | — | — | — | — | — | — | — |
| A83-01 | TGF-β inhibition (ALK4, 5, 7 inhibition) | — | — | — | — | — | — | — | — |
| LDN193189 | BMP inhibition (ALK2, 3 inhibition) | 1 | 1 | 1 | 1 | 1 | — | 1 | 1 |
| Dorsomorphin | BMP inhibition (ALK2, 3 inhibition) | 1 | 1 | — | 1 | 1 | 1 | 1 | 1 |
| Forskolin | CAMP induction | 7.5 | 7.5 | 7.5 | — | 7.5 | 7.5 | 7.5 | 7.5 |
| CHIR99021 | GSK3 inhibition | 1 | 1 | 1 | 1 | — | 1 | 1 | 1 |
| PD0325901 | Erk inhibition | 1 | 1 | 1 | 1 | 1 | 1 | — | 1 |
| Pifithrin-α | p53 inhibition | 5 | 5 | 5 | 5 | 5 | 5 | 5 | — |

TABLE 2

(Unit: μmol/L)

| Compound | Function | Comp. Ex. 1 | Comp. Ex. 2 | Comp. Ex. 3 | Comp. Ex. 4 |
|---|---|---|---|---|---|
| RepSox | TGF-β inhibition (Selective ALK5 inhibition) | — | — | — | — |
| SB431542 | TGF-β inhibition (ALK4, 5, 7 inhibition) | 2 | 2 | — | 2 |
| A83-01 | TGF-β inhibition (ALK4, 5, 7 inhibition) | — | — | 2 | — |
| LDN193189 | BMP inhibition (ALK2, 3 inhibition) | 1 | 1 | 1 | 1 |
| Dorsomorphin | BMP inhibition (ALK2, 3 inhibition) | — | 1 | 1 | 1 |
| Forskolin | cAMP induction | 7.5 | 7.5 | 7.5 | 7.5 |
| CHIR99021 | GSK3 inhibition | 1 | 1 | 1 | 1 |
| PD0325901 | Erk inhibition | 1 | 1 | 1 | 1 |
| Pifithrin-α | p53 inhibition | 5 | 5 | 5 | — |

(3) Results

Figure 1:
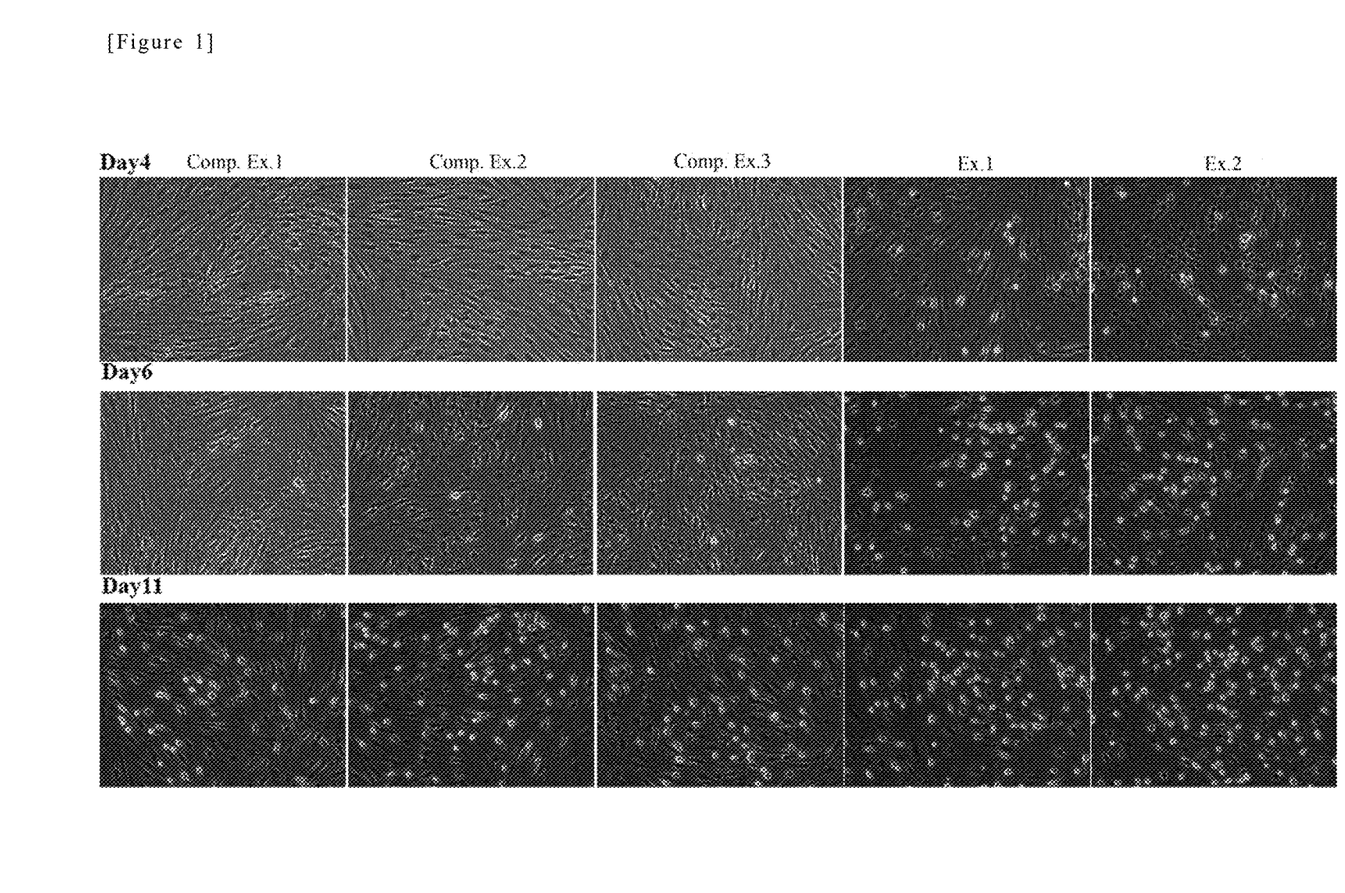
FIG. 1 A photograph of human fibroblasts after culture. Day 4, 6, and 11 show results on the fourth day, the sixth day, and the eleventh day, respectively, after initiation of culture.

The results of culturing according to (2) above are shown in FIGS. 1 to 5. As shown in FIG. 1, Examples 1 and 2 in which the culture was performed with a selective ALK5 inhibitor as a TGF-β inhibitor exhibited on the sixth day (Day 6) an inducing effect of neuron-like cells comparable to that of the eleventh day (Day 11) in Comparative Examples 1 to 3 in which the culture was performed with a wide range of ALK4, 5, 7 inhibitors as TGF-β inhibitors.

Figure 2:
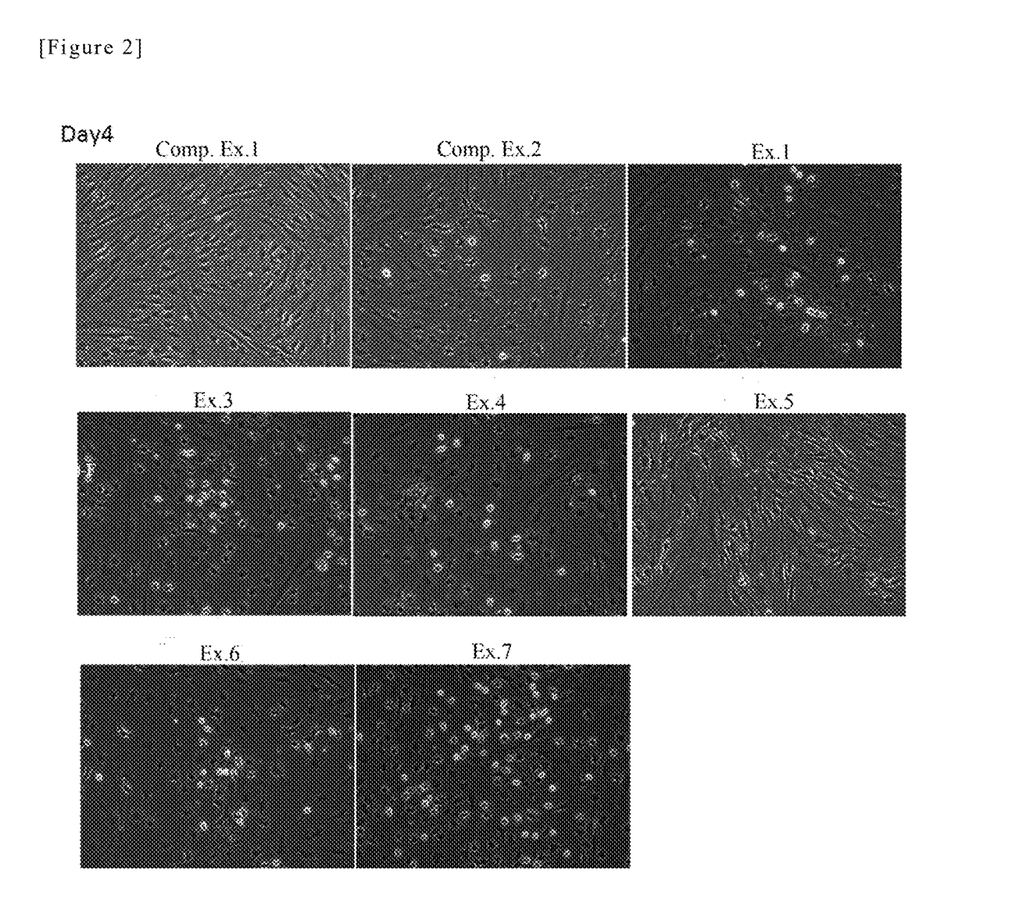
FIG. 2 A photograph of the cells on the fourth day after the start of culture.
Figure 3:
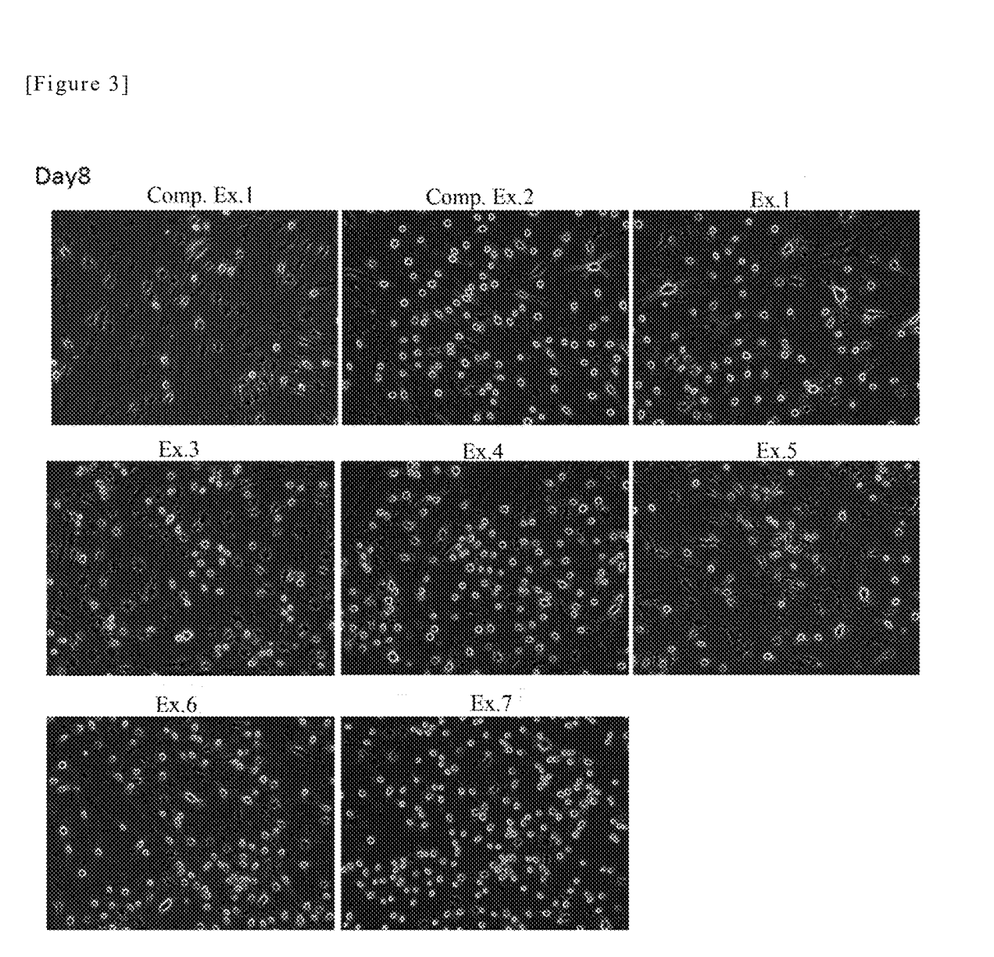
FIG. 3 A photograph of the cells on the eighth day after the start of culture.
Figure 5:
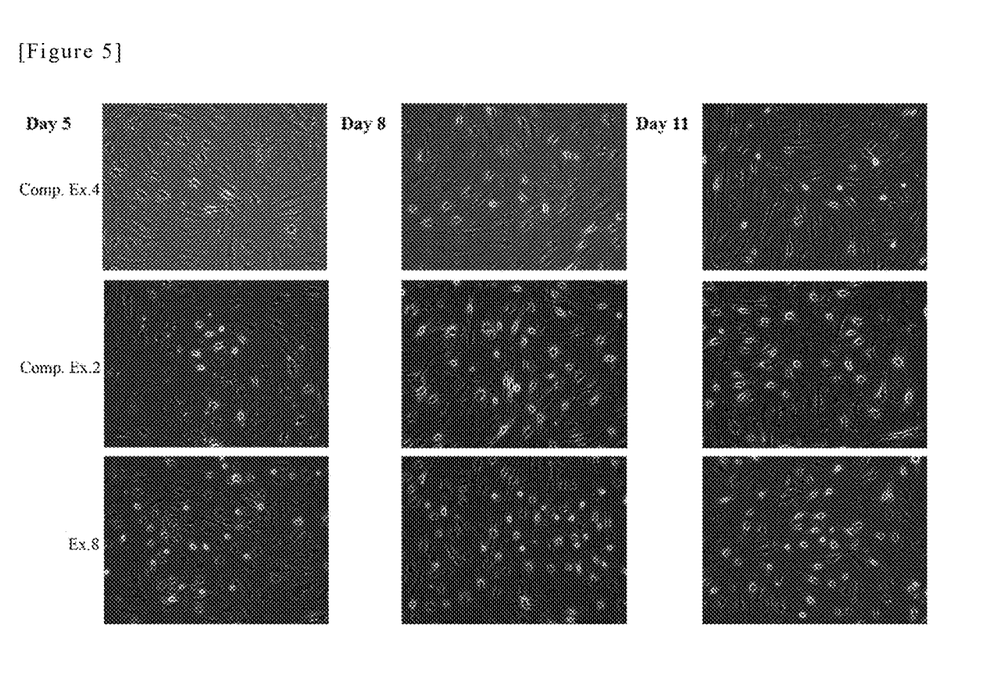
FIG. 5 A photograph of human fibroblasts after culture. The three figures of the upper row show the results of Comparative Example 4, the three figures of the middle row show the results of Comparative Example 2, and the three figures of the lower row show the results of Example 8. The three figures of the left column show the results on the fifth day (Day 5) after the start of culturing, the three figures of the middle column show the results on the eighth day (Day 8) after the start of culturing, and the three figures of the right column show the results on the eleventh day (Day 11) after the start of culturing.

As shown in FIGS. 2 and 3, when the culture was performed using a selective ALK5 inhibitor as a TGF-β inhibitor, it was found that inhibition of signal transduction by dorsomorphin was not required as in the result of Example 3. Further, as shown in FIG. 5, Comparative Example 2 in which the culture was performed in the presence of a p53 inhibitor showed higher induction efficiency than Comparative Example 4 in which the culture was performed in the absence of a p53 inhibitor, but when a selective ALK5 inhibitor was used as a TGF-β inhibitor, even in the absence of the p53 inhibitor as in Example 8, high induction efficiency was exhibited.

Figure 4:
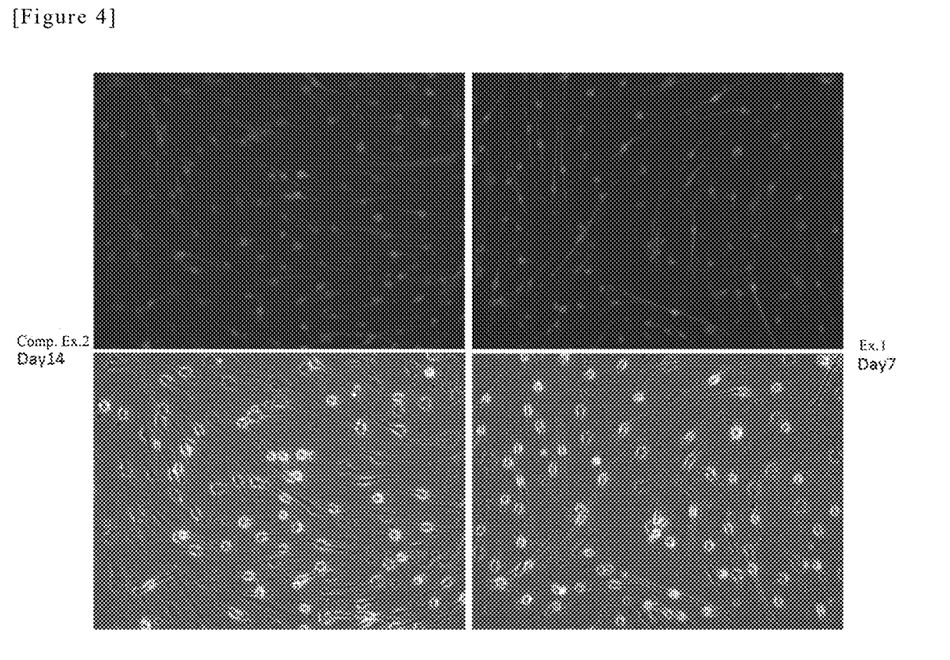
FIG. 4 A photograph of antibody-stained human fibroblasts after culture. The left two figures represent the results at the fourteenth day after the start of culture for Comparative Example 2, and the right two figures represent the results at the seventh day after the start of culture for Example 1, respectively.

Antibody staining with neuronal cell markers was then performed. At 14 days after the start of culture for Comparative Example 1, and at 7 days after the start of culture for Example 1, the cells were fixed with 2% paraformaldehyde, and then immunostaining was performed. Anti-Neuronal Class III β-Tubulin (TUJ1) antibody (Mouse anti-Tuj1: MMS-435P; formerly Covance (now Funakoshi); 1000-fold diluted) was used for staining. The results are shown in FIG. 4. Note that, since FIG. 4 is in gray scale, green and blue are not displayed, but in the actual original photograph, blue indicates nuclear staining with DAPI and green indicates staining of β3-tubulin.

As is apparent from FIG. 4, almost equivalent neuron-like cells were obtained at 7 days after the start of culture in Example 1 in which the culture was performed using a selective ALK5 inhibitor as a TGF-β inhibitor and at 14 days after the start of culture in Comparative Example 1 in which the culture was performed using a wide range of ALK4, 5, and 7 inhibitors as a TGF-β inhibitor.

The invention claimed is:

1. A process for producing a neuron-like cell by direct differentiation induction from a skin fibroblast, comprising a step of culturing the skin fibroblast in the presence of a TGF-β inhibitor, a BMP inhibitor, a cAMP inducer, and a GSK3 inhibitor and in the absence of a p53 inhibitor and a growth factor, wherein
   the TGF-β inhibitor comprises RepSox (CAS No: 446859-33-2),
   the BMP inhibitor comprises LDN193189 and dorsomorphin, and
   the process directly induces differentiation from the fibroblast to the neuron-like cell without generating a stem cell.

2. The process for producing a neuron-like cell according to claim 1, wherein the BMP inhibitor comprises an ALK2/3 inhibitor.

3. The process for producing a neuron-like cell according to claim 1, wherein the GSK3 inhibitor comprises CHIR99021 (CAS No: 252917-06-9).

4. The process for producing a neuron-like cell according to claim 1, wherein the skin fibroblast is cultured in the absence of a cytokine.

5. The process for producing a neuron-like cell according to claim 1, wherein the CAMP inducer comprises forskolin.

6. The process for producing a neuron-like cell according to claim 1, wherein the TGF-β inhibitor comprises an inhibitor which exclusively inhibits ALK5.

7. The process for producing a neuron-like cell according to claim 1, wherein the skin fibroblast is cultured in the absence of a histone deacetylase inhibitor.

8. The process for producing a neuron-like cell according to claim 7, wherein the histone deacetylase inhibitor is valproic acid.

* * * * *